United States Patent [19]
Rebrovic

[11] Patent Number: 5,420,316
[45] Date of Patent: May 30, 1995

[54] PROCESS FOR MAKING CARBOXYLIC ACIDS

[75] Inventor: Louis Rebrovic, Cincinnati, Ohio

[73] Assignee: Henkel Corporation, Plymouth Meeting, Pa.

[21] Appl. No.: 195,944

[22] Filed: Feb. 10, 1994

[51] Int. Cl.$^6$ .................. C07C 51/25; C07C 51/34
[52] U.S. Cl. .................. 554/121; 554/133; 562/413; 562/524; 562/544; 562/562
[58] Field of Search ............... 554/121, 133; 562/562, 562/524, 544, 413

[56] References Cited

U.S. PATENT DOCUMENTS 2,813,113  11/1957  Goebel et al. ............... 260/406
3,026,353   3/1962  Frank et al. ................. 260/531

OTHER PUBLICATIONS

Knops-Gerrits et al., *Nature*, 369, pp. 543–546 (1994).
Anal. Chem., 23, 541 (1951).

*Primary Examiner*—José G. Dees
*Assistant Examiner*—Barbara S. Frazier
*Attorney, Agent, or Firm*—Ernest G. Szoke; Wayne C. Jaeschke; John E. Drach

[57] ABSTRACT

A carboxylic acid is made by contacting an organic compound having at least one olefinic bond with ozone to form a mixture of ozonization products; contacting the mixture of ozonization products with oxygen to form a mixture of oxidation products; contacting the mixture of oxidation products with oxygen in the presence of an effective amount of a catalyst selected from the group consisting of a manganese-exchanged X-zeolite, a manganese-exchanged Y-zeolite, a manganese-exchanged A-zeolite, or a combination thereof to form said carboxylic acid.

17 Claims, No Drawings

PROCESS FOR MAKING CARBOXYLIC ACIDS

BACKGROUND OF THE INVENTION

1. Field of the Invention

This invention relates to an improved process for making carboxylic acids by ozonolysis of a compound having at least one olefinic bond and subsequent reaction of the ozonolysis products with oxygen in the presence of a solid phase manganese catalyst.

2. Description of the Related Art

The general chemical course of the reactions involved in the process according to this invention is well known. For example, it is well known that azelaic and pelargonic acids can be made by ozonolysis of oleic acid as described in U.S. Pat. No. 2,813,113, the entire contents of which are incorporated herein by reference. In general, the process involves the ozonization of olefinic compound to form a mixture of ozonides, treatment of the ozonides with an oxidizing agent such as hydrogen peroxide or oxygen to form a mixture of oxidation products, hereafter abbreviated as MOP. MOP is comprised of carboxylic acids and other carbonyl-containing species such as aldehydes and ketones. The combined concentration of aldehydes and ketones is expressed as a carbonyl value which is abbreviated as COV and has the units parts per million (ppm). The COV value of the oxidation products of the MOP must be reduced because the end users of the products of the process according to the invention have found that aldehydes and ketones interfere with subsequent reactions and/or produce color in the final products. For example, the process according to the invention is especially suitable for the manufacture of azelaic acid (1,9-nonanedicarboxylic acid). Azelaic acid is an important ingredient in such items as modified polyester fibers for apparel and carpeting, and engineering plastics. It is also used in urethane elastomers, polyester films and adhesives, plasticizers, and synthetic lubricants. Manufacturers of such products have found that small amounts of aldehydes and ketones can result in discoloration of the final products. It is very important, therefore, to reduce the amount of aldehydes and ketones present in azelaic acid to a minimum or eliminate them altogether.

The COV of the oxidation product mixture can be reduced to a minimum by further reaction with oxygen and preferably with oxygen in the presence of a transition metal ion catalyst such as cobalt and manganese. The COV reduction process will typically reduce the COV from a value of, for example, 6300 ppm to a value of 5800 ppm in 5 hours in the presence of oxygen and without manganese catalyst and from 6300 ppm to 2700 ppm in 5 hours with oxygen and with manganese catalyst. Prior to the present invention, the principal difficulty encountered with the use of manganese catalysts was that the manganese ion was typically used at a concentration of 1500 ppm and the soluble manganese ion invariably ended up in effluent waste streams. Since state and federal regulatory standards for manganese levels in effluent streams are being set at progressively lower values, the presence of the manganese ion in waste streams can present a major environmental problem.

The process according to the invention eliminates the problem of waste stream contamination by the use of manganese catalysts wherein the manganese ion is immobilized in the COV reduction process. Preferably, the manganese can be immobilized by incorporating it into a solid phase system such as an manganese-exchanged zeolite wherein other metal ions such as $Na^+$ have been exchanged by $Mn^{+2}$. A solid phase manganese catalyst such as $Mn^{+2}$-exchanged zeolite can be recycled repeatedly into the COV reduction process thereby reducing catalyst cost and eliminating manganese from the process effluent.

SUMMARY OF THE INVENTION

It has been surprisingly discovered that a carboxylic acid, which contains very small amounts of aldehydes and ketones, can be made by ozonization of an organic compound having at least one olefinic bond. The first step of the process comprises contacting an organic compound having at least one olefinic bond with ozone to form a mixture of ozonization products. This mixture of ozonization products is then contacted with oxygen to form a mixture of oxidation products having an unacceptably large amount of other carbonyl compounds such as aldehydes and ketones which is abbreviated as COV. The COV is reduced to an acceptable level by contacting the mixture of oxidation products with oxygen in the presence of a solid phase manganese catalyst such as a manganese-exchanged X-zeolite, a manganese-exchanged Y-zeolite, a manganese-exchanged A-zeolite, or a combination thereof to form a carboxylic acid having a low level of aldehydes and ketones.

DETAILED DESCRIPTION OF THE INVENTION

Other than in the claims and in the operating examples, or where otherwise indicated, all numbers expressing quantities of ingredients or reaction conditions used herein are to be understood as modified in all instances by the term "about".

The first step in the process according to the invention involves the reaction of an organic compound having at least one olefinic bond with ozone. The compound having at least one olefinic bond can be linear or cyclic. If the compound having at least one double bond is a linear alkene, then 2 carboxylic acids will be formed which may or may not be different depending upon the position of the double bond. For example, if 3-hexene is used, then 2 moles of propionic acid would be formed per mole of 3-hexene. If 2-hexene is used, then 1 mole of acetic acid and 1 mole of butyric acid will be formed per mole of 2-hexene.

If the compound having at least one double bond also contains a functional group, then the resulting carboxylic acid may also contain the same functional group as long as the functional group is not susceptible to reaction with ozone or other substances in the process such as oxygen.

If the compound having at least one olefinic bond also contains a carboxylic acid functionality, then the resulting product may contain 1 mole of a dicarboxylic acid and 1 mole of a mono-carboxylic acid per mole of starting olefin depending upon the structure of the starting compound. For example, if oleic acid is the compound having at least one olefinic bond, the product of the process according to the invention will produce one mole of pelargonic acid and one mole of azelaic acid per mole of oleic acid. The process according to the invention is particularly useful in making pelargonic and azelaic acids from oleic acid, especially technical grade oleic acid which is comprised of, in addition to a major amount of oleic acid, a $C_{12}$ saturated carboxylic acid; a $C_{14}$ saturated carboxylic acid; a $C_{14}$ monounsaturated carboxylic acid; a $C_{16}$ saturated carboxylic acid; a $C_{16}$ monounsaturated carboxylic acid; a $C_{17}$ saturated carboxylic acid; a $C_{18}$ saturated carboxylic acid; a $C_{18}$ carboxylic acid having two double bonds; $C_{18}$ carboxylic acid having three double bonds.

If a cyclic mono-olefin is used as the compound which contains at least one olefinic bond a dicarboxylic acid will be formed in the process according to the invention. For example, if cyclohexene is used then 1 mole of adipic acid will be formed per mole of cyclohexene. If a cyclic, non-conjugated di-olefin is used as the compound which contains at least one olefinic bond, 2 dicarboxylic acids will be formed which may or may not differ depending upon the relative positions of the double bonds. For example, if 1,4-cyclohexadiene is used, then 2 moles of malonic acid per mole of 1,4-cyclohexadiene will be formed. If 1,3-cyclohexadiene is used, then 1 mole of succinic acid and some oxalic acid will be formed per mole of 1,3-cyclohexadiene.

The ozone used may be, and preferably is, mixed with diatomic oxygen and/or non reactive gases such as nitrogen during its mixing with a fluid containing unsaturated molecules as part of a process according to this invention. With increasing preference, the gas mixture supplied for reaction contains from 0.5 to 14, from 1 to 8, or from 2 to 6 volume percent (hereinafter "v/o") of ozone; and, independently, with increasing preference, the same gas mixture contains from 99.5 to 86, from 99 to 92, or from 98 to 94 v/o of diatomic oxygen. Preferably the fluid containing the unsaturated molecules to be converted to carboxylic acids is a liquid and is mixed with the gas containing ozone by some means for promoting efficient contact; such means are generally known in the art.

The second step of the process according to the invention involves the reaction of the mixture of ozonization products formed in the first step with oxygen to produce a mixture of oxidation products (MOP). This step can be carried out by contacting the ozonization products with oxygen or, preferably, contacting the ozonization products with oxygen in the presence of a base such as sodium hydroxide. Most preferably, the ozonization products are contacted in the presence of a solid phase selected from X and Y type zeolites, preferably X type zeolites, most preferably sodium or potassium zeolite X as described in copending application Ser. No. 07/768,287, filed on Sept. 9, 1991, the entire contents of which are incorporated herein by reference. An X type zeolite has the general crystal structure of faujasite and an atomic ratio of silicon to aluminum atoms in the range from 1 to 1.5; a Y type zeolite is otherwise similar but has an atomic ratio of silicon to aluminum atoms in the range from >1.5 to 3.

The amount of solid phase catalyst which can be used in the second step in the process according to the invention is any amount which will decrease the ozonide concentration to about 0.25 mmol O-O/gram in a practical time period (see Example 10). The effective amount can be varied within wide limits. If the catalyst is used in finely divided form and continuously stirred with the fluid reagents during reaction a volume that includes all the ozonides being oxidized in a batch process, as is preferred in one embodiment of the invention, the amount of catalyst used should be, with increasing preference, from 0.1 to 50, from 0.5 to 25, or from 1 to 16, w/o of the amount of the total of olefinic groups and/or ozonides thereof present in the fluid reaction mixture that is mixed together with the finely divided catalyst. In another embodiment, preferred for large scale operations, the catalyst is used in a fixed bed through which the fluid reaction mixture containing ozonides is passed. In this embodiment, the amount of catalyst used is, with increasing preference, from 1 to 250, from 50 to 200, or from 75 to 150, w/o of the amount of the total of the olefinic groups and/or ozonides thereof present in the amount of fluid reaction mixture passed through the fixed bed in one hour.

The third step of the process according to the invention comprises the reaction of the MOP with oxygen in the presence of a solid phase manganese catalyst. The solid phase manganese catalyst can be any solid phase substance which is insoluble in the reaction medium and having $Mn^{+2}$ ions which are part of the solid substance such that the $Mn^{+2}$ ions will not enter the reaction medium. For example, the solid phase manganese catalyst can be a $Mn^{+2}$-exchanged zeolite made by exchanging $Mn^{+2}$ ions for other metal ions such as $Na^+$ to form a $Mn^{+2}$-exchanged zeolite. Examples of such zeolites include but are not limited to $Mn^{+2}$-exchanged A-zeolite, a $Mn^{+2}$-exchanged X-zeolite, a $Mn^{+2}$-exchanged Y-zeolite. Combinations of $Mn^{+2}$-exchanged zeolites can also be used in the process according to the invention. Na-X and Na-Y zeolites can be purchased, for example, from UOP, P.O. Box 65, Tarrytown, N.Y., 10591. Na-A zeolites can be purchased, for example, from Miles Inc., Mobay Rd., Pittsburgh, Pa. 15205. The solid phase manganese catalyst can also be a polymer-bound $Mn^{+2}$ catalyst made by incorporating the $Mn^{+2}$ ion into a polymer-supported catalyst such as an ion exchange resin.

The preferred solid phase manganese catalysts are $Mn^{+2}$-exchanged A-zeolites, $Mn^{+2}$-exchanged X-zeolites, and $Mn^{+2}$-exchanged Y-zeolites. The most preferred solid phase manganese catalysts are $Mn^{+2}$-exchanged X-zeolites, and $Mn^{+2}$-exchanged Y-zeolites. The $Mn^{+2}$-exchanged zeolites can be prepared by the method as set forth in Example 1. The amount of solid phase manganese catalyst that can be used in the process according to the invention determines the rate at which the COV is reduced to a desired minimum level. The rate at which the COV is decreased to an acceptable level is a function of the amount of solid phase manganese catalyst relative to the amount of MOP. Any practical amount of solid phase manganese catalyst will be effective in decreasing the COV to an acceptable level. However, the greater the amount of solid phase manganese catalyst the greater the rate of COV reduction. An effective amount is any amount which will decrease the COV to an acceptable level and can range from 1% or less to over 1000%. The data presented in Example 8 is one example of the sensitivity of the relative rates of decrease in the COV level on the weight % of $Mn^{+2}$-exchanged X-zeolite based on the weight of MOP. The term catalyst loading is defined as the weight percent of solid phase manganese catalyst based on the weight of MOP. A catalyst loading which exceeds very large numbers such as 1000% would produce a very large rate of COV decrease. Such a large catalyst loading could be achieved by means of the process hardware design. For example, a reaction zone could be constructed wherein the MOP is passed through a fixed bed of solid phase manganese catalyst such that the catalyst loading is very large. This could be achieved by passing a stream of liquid MOP through a column packed with a solid phase manganese catalyst such that a relatively small weight of MOP is contacted by a very large amount of solid phase manganese catalyst. The stream of liquid MOP could also be repeatedly recycled through the solid phase manganese catalyst until a minimum COV is reached. Other methods of achieving a large catalyst loading similar to those set forth above will be apparent to those skilled in the art.

The amount of oxygen which may be used to contact the MOP in the presence of the solid phase manganese catalyst can be any amount up to and including complete oxygen saturation of the entire reaction mixture.

The following examples are meant to illustrate but not to limit the invention.

EXAMPLE 1

Preparation of $Mn^{+2}$-exchanged X- or Y-zeolite

To 125 ml of a 1.0 Molar aqueous solution of manganese acetate tetrahydrate was added 15 grams of either Na-X or Na-Y zeolite. The mixture was slowly stirred and heated at 90° C. for 5 hours afterwhich the exchanged zeolite was filtered and washed twice with 100 ml of water. The zeolite was then allowed to sit overnight in a crystallization dish and was then subjected to 30 inches of vacuum at 170° C. for 3.5 hours. The zeolite was used as is.

EXAMPLE 2

Preparation of Mixed Oxidation Products (MOP)

A mixture comprised of 3 parts of technical oleic acid which consisted of the following carboxylic acids: 0.42% $C_{12}$; 2.7% $C_{14}$; 0.86% $C_{14}:1$; 6.3% $C_{16}$; 4.6% $C_{16}:1$; 0.93% $C_{17}$; 2.8 $C_{18}$; 71.8% $C_{18}:1$; 8.3% $C_{18}:2$; 0.58% $C_{18}:3$ and 1 part of technical pelargonic acid was treated with a gas containing 5 v/o of ozone with the balance $O_2$ at a rate to supply 0.00644 mmole of $O_3$ per minute of oleic acid present in the acid mixture per minute for 2.5–3.0 hours at 23°–25° C. The gas was supplied through a conventional sparger with a pore size of 147–174 μm. Afterwards, nitrogen gas was sparged into the post-reaction mixture for 15 minutes, in order to free the mixture substantially from either form of gaseous oxygen.

An amount of 23 grams of a mixture prepared as described above was placed together with 0.30 g of a Na-X Zeolite catalyst were placed in a reactor. The reactor was placed in a temperature controlled water bath and initially sparged with nitrogen while the temperature was maintained 10° below the desired reaction temperature of 60° C. The temperature controller for the water bath was then set to increase the temperature up to the desired reaction temperature. When the desired reaction temperature was reached in the water bath, the gas flow was changed from nitrogen to oxygen at a rate of 350 ml/min. The reaction was continued until the peroxide content reached about 0.25 mmol O-O/gram by the method described in Example 10.

EXAMPLE 3

Analytical Procedure for Aldehyde & Ketone Determination in MOP

The MOP analysis determines the total of all the aldehydes and ketones by means of a method set forth in Anal. Chem., 23, 541 (1951) except that 7-oxooctanoic acid was used to prepare a calibration table. In this method, the carbonyl groups of the aldehydes and ketones are converted into their 2,4-dinitrophenylhydrazones and then are converted into their quinoidal ion in base. The amount of the 2,4-dinitrophenylhydrazones are determined spectrophotometrically at 480 nm. The total amount of aldehyde and ketone was expressed as the carbonyl value, COV, and has the units parts per million.

EXAMPLE 4

General Reaction Procedure

All reactions were conducted in a custom built apparatus which is a 22×2 cm vertical glass tube having a rounded and closed bottom. The bottom of a 100 ml round bottom flask fitted with a conventional course frit gas sparger tube for oxygen introduction, a condenser, rubber septum, and a thermocouple is fused to the top end of the tube. The gas sparger tube extended to the bottom of the vertical glass tube. The tube portion of the reaction apparatus was immersed in an oil bath. About 30 grams of MOP from the ozonolysis step of the process were added to the reaction apparatus followed by the appropriate amount of $Mn^{+2}$-exchanged zeolite and then the remaining MOP was added for a total MOP of about 60 grams. In the charged reactor, the oxygen sparger tube is at the bottom of the vertical glass tube portion of the reaction apparatus and below the $Mn^{+2}$-exchanged zeolite and the MOP. The assembled, charged reactor is immersed in a 120° C. oil bath. During the time required for the contents of the reactor to come to 120° C., nitrogen was introduced through the sparger tube to disperse the zeolite in the MOP. When the reactor contents reach 117° C., oxygen replaced nitrogen at a rate of 1250 ml/min. Samples were taken for COV analysis as described in Example 2 at various time intervals.

The MOP that was used in each of the Examples was obtained from a commercial scale plant for the production of azelaic and pelargonic acids from the ozonolysis of oleic acid as described in Example 2.

EXAMPLE 5

Comparative COV Reduction
With and Without $Mn^{+2}$-Exchanged Zeolite

Two oxidation reactions, one with $Mn^{+2}$-exchanged zeolite catalyst and one without, were carried out according to the method described in Example 3 except that the oxygen flow rate was 2500 ml/min and 6.0 grams of $Mn^{+2}$-exchanged X-zeolite was used so that the catalyst loading was 10% by weight of MOP. The following table shows the COV values as a function of time in hours.

| No catalyst | | 10% $Mn^{+2}$-exchanged zeolite | |
| --- | --- | --- | --- |
| Time (hours) | COV (ppm) | Time (hours) | COV (ppm) |
| 0.00 | 6302 | 0.00 | 6283 |
| 0.50 | 6275 | 0.25 | 6238 |
| 1.00 | 5787 | 0.50 | 5515 |
| 1.50 | 6345 | 1.00 | 5396 |
| 3.00 | 6388 | 2.00 | 4371 |
| 4.00 | 6414 | 3.00 | 3974 |
| 5.00 | 5861 | 5.00 | 2695 |
| | | 10.00 | 1291 |

EXAMPLE 6

Recycle of $Mn^{+2}$-Exchanged X-Zeolite Catalyst

Two oxidation reactions were carried wherein $Mn^{+2}$-exchanged X-zeolite catalyst from a first reaction was reused in a second reaction. The reactions were carried out according to the method described in Example 3 except that the oxygen flow rate was 2500 ml/min and 6.0 grams of $Mn^{+2}$-exchanged X-zeolite were used. The COV data as a function of time is shown in the following table.

| Reaction #1 | | Reaction #2 | |
|---|---|---|---|
| Time (hours) | COV (ppm) | Time (hours) | COV (ppm) |
| 0.00 | 7896 | 0.00 | 7896 |
| 0.25 | 6490 | 0.25 | 5080 |
| 0.50 | 6100 | 0.50 | 4554 |
| 1.00 | 5241 | 1.00 | 3551 |
| 2.50 | 2117 | 2.00 | 2204 |
| 4.00 | 899 | 3.00 | 1567 |
| 5.00 | 419 | 5.00 | 887 |
| 10.00 | 391 | 10.00 | 660 |

EXAMPLE 7

Recycle of $Mn^{+2}$-Exchanged Y-Zeolite Catalyst

The procedure described in Example 5 was repeated except that $Mn^{+2}$-exchanged Y-zeolite catalyst was used. The COV data as a function of time is shown in the following table.

| Reaction #1 | | Reaction #2 | |
|---|---|---|---|
| Time (hours) | COV (ppm) | Time (hours) | COV (ppm) |
| 0.00 | 7896 | 0.00 | 7896 |
| 0.50 | 5005 | 0.50 | 3436 |
| 1.00 | 4363 | 1.00 | 3083 |
| 2.00 | 2652 | 2.00 | 2029 |
| 3.00 | 1737 | 4.00 | 1521 |
| 5.00 | 1491 | 5.00 | 1239 |
| 10.00 | 976 | 10.00 | 855 |

EXAMPLE 8

Comparative COV Reduction

For Different Catalyst Loading of $Mn^{+2}$-Exchanged X-Zeolite

The COV reduction for two oxidation reactions wherein the catalyst loading was different were compared. The reactions were carried out according to the method described in Example 3 except that the oxygen flow rate was 2500 ml/min. The catalyst loading for the 10% run was 6.0 grams of $Mn^{+2}$-exchanged X-zeolite were used. For the 20% run, the finished reaction mixture from run #1 was decanted, 60.0 grams of MOP were added followed by an additional 6.0 grams of $Mn^{+2}$-exchanged X-zeolite catalyst. The COV data as a function of time for the two runs is shown in the following table.

| 10% catalyst load | | 20% catalyst load | |
|---|---|---|---|
| Time (hours) | COV (ppm) | Time (hours) | COV (ppm) |
| 0.00 | 6743 | 0.00 | 6743 |
| 1.00 | 4767 | 1.00 | 3593 |
| 2.00 | 3821 | 2.00 | 2414 |
| 3.00 | 3065 | 3.00 | 1613 |
| 4.00 | 2260 | 4.00 | 1280 |
| 6.00 | 1432 | 5.00 | 1018 |
| | | 6.00 | 844 |

EXAMPLE 9

Repeated Recycle of $Mn^{+2}$-Exchanged Y-Zeolite Catalyst

This example is an illustration of the lifetime of a $Mn^{+2}$-exchanged Y-zeolite catalyst in a process according to the invention. The procedure described in Example 3 was repeated except that 7.0 grams of $Mn^{+2}$-exchanged Y-zeolite were used. The initial catalyst/MOP weight ratio was initially 12%. The catalyst was reused 12 times so that the total catalyst/MOP weight ratio was less than 1%. The COV data at the end of 9 hours for each run is given in the following table.

| Run # | COV After 9 Hours |
|---|---|
| 1 | 1779 |
| 2 | 1956 |
| 3 | 957 |
| 4 | 819 |
| 5 | 773 |
| 6 | 650 |
| 7 | 720 |
| 8 | 695 |
| 9 | 691 |
| 10 | 647 |
| 11 | 577 |
| 12 | 680 |

EXAMPLE 10

Peroxide Analysis by Iodometric Titration

Samples of approximately 0.15 to 0.20 g were weighed accurately to three decimal places in a small glass weighing cup and then dropped into a 125 ml iodine flask that was constantly purged with $N_2$. To this was added 10 ml of $CHCl_3$, 2.0 ml of saturated KI and 15 ml of glacial acetic acid. The $N_2$ purge was stopped and the flask immediately stoppered and swirled. The flask was allowed to sit in the dark for 25 minutes and then 50 ml of water was added. The mixture was then titrated with 0.0500M $Na_2S_2O_3$ using a starch indicator. The following formula gives the number of mmoles of —O—O—(peroxide)/gram sample:

$$\frac{\text{mmole} - O - O -}{\text{sample}} = \frac{\text{Volume}_{Na_2S_2O_3} \times 0.0500 \, M_{Na_2S_2O_3}}{2 \times \text{Sample weight}}$$

What is claimed is:

1. A process for making a carboxylic acid comprising: (1) contacting an organic compound having at least one olefinic bond with ozone to form a mixture of ozonization products; (2) contacting said mixture of ozonization products with oxygen to form a mixture of oxidation products; (3) contacting said mixture of oxidation products with oxygen in the presence of an effective amount of a catalyst selected from the group consisting of a manganese-exchanged X-zeolite, a manganese-exchanged Y-zeolite, a manganese-exchanged A-zeolite, or a combination thereof to form said carboxylic acid.

2. The process of claim 1 wherein said compound having at least one olefinic bond is oleic acid.

3. The process of claim 1 wherein said catalyst is a manganese-exchanged X-zeolite.

4. The process of claim 1 wherein said catalyst is a manganese-exchanged Y-zeolite.

5. The process of claim 1 wherein step (2) is carried out in the presence of an effective amount of an X or Y type zeolite.

6. The process of claim 1 further comprising the step of separating said carboxylic acid from said catalyst and recycling said catalyst.

7. A process for making a mixture of azelaic and pelargonic acids comprising: (1) contacting oleic acid with ozone to form a mixture of ozonization -products;

(2) contacting said mixture of ozonization products with oxygen to form a mixture of oxidation products; (3) contacting said mixture of oxidation products with oxygen in the presence of an effective amount of catalyst selected from the group consisting of a manganese-exchanged X-zeolite, a manganese-exchanged Y-zeolite, a manganese-exchanged A-zeolite, or a combination thereof to form said mixture of azelaic and pelargonic acids.

8. The process of claim 7 wherein said oleic acid is a technical grade comprised of, in addition to oleic acid, a $C_{12}$ saturated carboxylic acid; a $C_{14}$ saturated carboxylic acid; a $C_{14}$ monounsaturated carboxylic acid; a $C_{16}$ saturated carboxylic acid; a $C_{16}$ monounsaturated; a $C_{17}$ saturated carboxylic acid; a $C_{18}$ saturated carboxylic acid; a $C_{18}$ carboxylic acid having two double bonds; $C_{18}$ carboxylic acid having three double bonds.

9. The process of claim 7 wherein said catalyst is a manganese-exchanged X-zeolite.

10. The process of claim 7 wherein said catalyst is a manganese-exchanged Y-zeolite.

11. The process of claim 7 wherein step (2) is carried out in the presence of an effective amount of an X or Y type zeolite.

12. The process of claim 7 further comprising the step of separating said mixture of azelaic and pelargonic acids from said catalyst and recycling said catalyst.

13. A process for making a mixture of azelaic and pelargonic acids comprising: (1) contacting oleic acid with ozone to form a mixture of ozonization products; (2) contacting said mixture of ozonization products with oxygen in the presence of an effective amount of an X or Y type zeolite to form a mixture of oxidation products; (3) contacting said mixture of oxidation products with oxygen in the presence of an effective amount of catalyst selected from the group consisting of a manganese-exchanged X-zeolite, a manganese-exchanged Y-zeolite, a manganese-exchanged A-zeolite, or a combination thereof to form said mixture of azelaic and pelargonic acids.

14. The process of claim 13 wherein said oleic acid is a technical grade comprised of, in addition to oleic acid, a $C_{12}$ saturated carboxylic acid; a $C_{14}$ saturated carboxylic acid; a $C_{14}$ monounsaturated carboxylic acid; a $C_{16}$ saturated carboxylic acid; a $C_{16}$ monounsaturated; a $C_{17}$ saturated carboxylic acid; a $C_{18}$ saturated carboxylic acid; a $C_{18}$ carboxylic acid having two double bonds; $C_{18}$ carboxylic acid having three double bonds.

15. The process of claim 13 wherein said catalyst is a manganese-exchanged X-zeolite.

16. The process of claim 13 wherein said catalyst is a manganese-exchanged Y-zeolite.

17. The process of claim 13 further comprising the step of separating said mixture of azelaic and pelargonic acids from said catalyst and recycling said catalyst.

* * * * *